(12) United States Patent
Daerr et al.

(10) Patent No.: US 12,073,491 B2
(45) Date of Patent: Aug. 27, 2024

(54) ENERGY WEIGHTING OF PHOTON COUNTS FOR CONVENTIONAL IMAGING

(71) Applicant: KONINKLIJKE PHILIPS N.V., Eindhoven (NL)

(72) Inventors: Heiner Daerr, Hamburg (DE); Artur Sossin, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 480 days.

(21) Appl. No.: 17/312,036

(22) PCT Filed: Dec. 9, 2019

(86) PCT No.: PCT/EP2019/084109
§ 371 (c)(1),
(2) Date: Jun. 9, 2021

(87) PCT Pub. No.: WO2020/120344
PCT Pub. Date: Jun. 18, 2020

(65) Prior Publication Data
US 2022/0028127 A1    Jan. 27, 2022

(30) Foreign Application Priority Data

Dec. 11, 2018   (EP) ..................................... 18211666

(51) Int. Cl.
*G01T 1/36* (2006.01)
*A61B 6/03* (2006.01)
(Continued)

(52) U.S. Cl.
CPC .......... *G06T 11/003* (2013.01); *A61B 6/4241* (2013.01); *A61B 6/585* (2013.01);
(Continued)

(58) Field of Classification Search
USPC ...... 250/251–271, 302–395, 559.02–559.49; 378/1–98.12, 167–207; 382/100–103,
(Continued)

(56) References Cited

U.S. PATENT DOCUMENTS 7,433,443 B1   10/2008   Tkaczyk
8,194,820 B2   6/2012    Wang
(Continued)

FOREIGN PATENT DOCUMENTS

CN   103472074 A   12/2013
EP   3062093 A1   8/2016
(Continued)

OTHER PUBLICATIONS

Roessl Ewald, Photon-Counting Computed Tomography, Jan. 4, 2018 (Year: 2018).*
(Continued)

*Primary Examiner* — Marcellus J Augustin
(74) *Attorney, Agent, or Firm* — Larry Liberchuk

(57) ABSTRACT

A System for image processing, comprising an input interface (IN) for receiving energy resolved count data generated by a photon-counting detector (PCD) with at least 2 energy bin but preferable more than two. A count data transformer (DT) of the system is configured to perform a transformation operation to transform the energy resolved count data into transformed count data, the operation including applying one or more weights to the count data, the weights previously obtained based on i) calibration image data for the or a photon-counting detector and ii) calibration image data for an energy integrating detector. A data convertor component (CC) is configured to convert the transformed count data into through-material path length data. The system allows emulating an energy integrating detector.

8 Claims, 8 Drawing Sheets

(51) Int. Cl.
*A61B 6/42* (2024.01)
*A61B 6/58* (2024.01)
*G01T 1/24* (2006.01)
*G06T 11/00* (2006.01)

(52) U.S. Cl.
CPC ............ *G01T 1/24* (2013.01); *G06T 2200/24* (2013.01); *G06T 2207/10116* (2013.01)

(58) Field of Classification Search
USPC .................................................. 382/159–224
See application file for complete search history.

(56) References Cited

U.S. PATENT DOCUMENTS

| | | | |
|---|---|---|---|
| 9,437,016 | B2 | 9/2016 | Rigie |
| 9,579,075 | B2 | 2/2017 | Besson |
| 9,588,239 | B2 | 3/2017 | Abraham |
| 9,693,743 | B2 * | 7/2017 | Arakita ............... G01T 1/20182 |
| 10,497,152 | B2 | 12/2019 | Miyazaki |
| 10,724,969 | B2 | 7/2020 | Xing |
| 2010/0027743 | A1 | 2/2010 | Engel |
| 2015/0257722 | A1 | 9/2015 | Wang |
| 2017/0212250 | A1 | 7/2017 | Jin |
| 2018/0068464 | A1 | 3/2018 | Gronberg |
| 2019/0319393 | A1 * | 10/2019 | Zhou .................. H01R 13/5045 |
| 2020/0138386 | A1 * | 5/2020 | Zimmerman .......... A61B 6/482 |

FOREIGN PATENT DOCUMENTS

| | | |
|---|---|---|
| WO | WO2018002226 A1 | 1/2018 |
| WO | WO2018111164 A1 | 6/2018 |

OTHER PUBLICATIONS

PCT International Search Report, International application No. PCT/EP2019/084109, Mar. 6, 2020.
Hans Bornefalk et al., "Synthetic Hounsfield Units from Spectral CT Data", Physics in Medicine and Biology, Institute of Physics Publishing, Bristol GB, vol. 57, No. 7, Mar. 21, 2012 (Mar. 21, 2012), pp. N83-N87, XP020220777.
Alvarez R. et al., "Estimator for Photon Counting Energy Selective X-Ray Imaging with Multi-Bin Pulse Height Analysis", Medical Physics, 38 (5), May 2011.
Metropolis N. et al., "Equation of State Calculations by Fast Computing Machines", Journal of Chemical Physics, vol. 21, issue 6, p. 1087, Jun. 1953.
Knoll G.F. et al., "Counting Statistics and Error Prediction", Radiation Detection and Measurement, John Wiley & Sons; 4th edition, Chapter 3, pp. 65-104, Sep. 24, 2010.
Knoll G.F. et al., "Pulse Shaping, Counting, and Timing", Radiation Detection and Measurement, John Wiley & Sons; 4th edition, Chapter 11, pp. 625-704, Sep. 24, 2010.

* cited by examiner

ENERGY WEIGHTING OF PHOTON COUNTS FOR CONVENTIONAL IMAGING

FIELD OF THE INVENTION

The invention relates to a system for image processing, to an imaging arrangement, to methods of image processing, to a method of calibration, to a computer program element, and to a computer-readable medium.

BACKGROUND OF THE INVENTION

X-ray imaging is an important tool to learn structural details of the internals of objects in a non-destructive manner. Chief applications are in the medical field. CT (computed tomography) imaging for instance allow obtaining detailed cross sectional images of a patient's anatomy.

An X-ray imaging apparatus, such as a CT scanner, includes a detector configured to detect x-radiation after passage through the object or patient to be imaged. A types of X-ray detectors include energy integrating detectors. Energy integrating detectors have been used for many decades and represent the conventional standard on which generations of medical staff have been trained on. In X-ray imaging, an X-ray beam, including X-ray photons of different energies, passed through the patient or object and is the detected at the detector. Energy integrated detectors measure the total energy deposited by the X-ray photons at detector pixels after passage through patient tissue. In conventional CT, the detected data may be converted into Hounsfield unit values. Although useful in many instances, energy integrated detectors do not usually allow soft tissue discrimination with a sufficiently high sensitivity as may be required in many medical applications like oncology and the Hounsfield unit scale is not without problems as its interpretation may depend on the surrounding anatomy.

To address these issues among others, a new generation of detectors has emerged called energy resolving of photon counting detectors. These detectors are capable of analyzing the incoming X-ray photons into energy levels. Specifically, these detectors count how many photons fall into each energy level. In other words, they are capable of recording an approximation of the spectrum of the transmitted X-ray beam. The fineness of the approximation may depend on the number of energy levels considered. This count data as recorded by the photon counting detectors forms spectral information and can be harvested in many ways to produce new types of imagery. The imagery including material specific maps, virtual mono-chromatic images and others.

Acceptance of photon counting detectors in the medical community however might be relatively low because, as mentioned above, generations of medical students have been trained on Hounsfield unit type imagery derived from energy integrating detectors.

SUMMARY OF THE INVENTION

There may therefore be a need to improve comparability between imagery obtainable using a photon counting detector imager and imagery obtainable using an energy integrating detector imager.

The object of the present invention is solved by the subject matter of the independent claims where further embodiments are incorporated in the dependent claims. It should be noted that the following described aspect of the invention equally applies to the imaging arrangement, to the methods of image processing, to the method of calibration, to the computer program element, and to the computer-readable medium.

According to a first aspect of the invention there is provided a system for image processing, comprising:

an input interface for receiving energy resolved count data generated by a photon-counting detector;

a count data transformer configured to perform a transformation operation to transform the energy resolved count data into transformed count data, the operation including applying one or more weights to the count data, the weights previously obtained based on i) calibration data for the or a photon-counting detector and ii) calibration data for an energy integrating detector; and an output interface for outputting the transformed count data.

According to one embodiment, the system comprises a data convertor component configured to convert the count data into through-material path length data. In other words, counts per pixel are converted into a respective path length through a reference material. More than one material type may be used. According to one embodiment, the reference material for the material path lengths into which the conversion component converts into, may be based on water or a material(s) having a similar radio-density.

The weights are preferably precomputed.

The calibration data for the photon-counting detector ("PCD") may include projection count data obtained in a calibration procedure using the PCD.

The calibration data for the energy integrating detector (EID") may include projection data or, preferably, image data reconstructed therefrom. The data is obtained in a calibration procedure using the EID.

The two calibration procedures may include imaging a test body, such as an imaging phantom, using the two detector types, respectively.

Alternatively, the weights may be obtained theoretically through simulation for instance.

According to one embodiment, the system includes a reconstructor configured to reconstruct the through-material path length data into image data. The image data may be displayed on a display device.

The proposed computerized system allows cross-detector image adaption and comparability. The system allows using the photon counting detector to "emulate" the imagery obtainable though a given energy integrating detector. The imagery that can be reconstructed from projection data of the two different detector types becomes better comparable. For instance, in CT embodiments, the converted image data emulate Hounsfield unit (HU) based imagery obtainable when using the energy integrating detector.

According to one embodiment, system comprises a user interface that is configured to allow a user to change at least one of the weights.

According to one embodiment, the imaging arrangement, comprises a system as per any one of the previous claims, and an imaging apparatus having the photon-counting detector.

According another aspect there is provided a method of image processing, comprising:

receiving energy resolved count data generated by a photon-counting detector;

transforming the energy resolved count data into transformed count data, the operation including applying one or more weights to the count data, the weights previously obtained based on i) calibration data for the or a photon-counting detector and ii) image data for an energy integrating detector; and outputting the transformed count data.

According another aspect there is provided a method of calibration, comprising:

receiving energy-resolved calibration count data for a photon-counting detector;

receiving calibration image data for an energy-integrating detector; and adjusting one or more weights applicable to the energy-resolved count data so as to fit image data derivable from the weighted count data to the calibration image data for the energy-integrating detector; and outputting the one or more weights.

The calibration image data and the calibration count data relate to the same phantom or test body. The weights are adjusted, preferably (but necessarily) iteratively in an automatic optimization procedure, until the image reconstructed from the count data corresponds, that is "looks like", the calibration image data for the energy-integrating detector. The correspondence can be quantified by a similarity measure. The calibration image data for the energy-integrating detector includes image data reconstructed from projection data recorded by the EID.

Alternatively, or in addition to the determining of the weights automatically through this optimization, there is, in embodiments, a user interface allowing the user to change/adjust the weights to fine-tune or manually perform the adaption.

According another aspect there is provided computerized system configured to perform the calibration method.

According to one embodiment, the energy-resolved calibration count data and/or the calibration image data is obtained based on exposing a sample body to X-radiation.

According another aspect there is provided a computer program element, which, when being executed by at least one processing unit, is adapted to cause the processing unit to perform the method as per any one of the above mentioned embodiments.

According another aspect there is provided a computer readable medium having stored thereon the program element.

BRIEF DESCRIPTION OF THE DRAWINGS

Exemplary embodiments of the invention will now be described with reference to the following drawings, with like reference signs indicating like components, wherein.

DETAILED DESCRIPTION OF EMBODIMENTS

Figure 1:
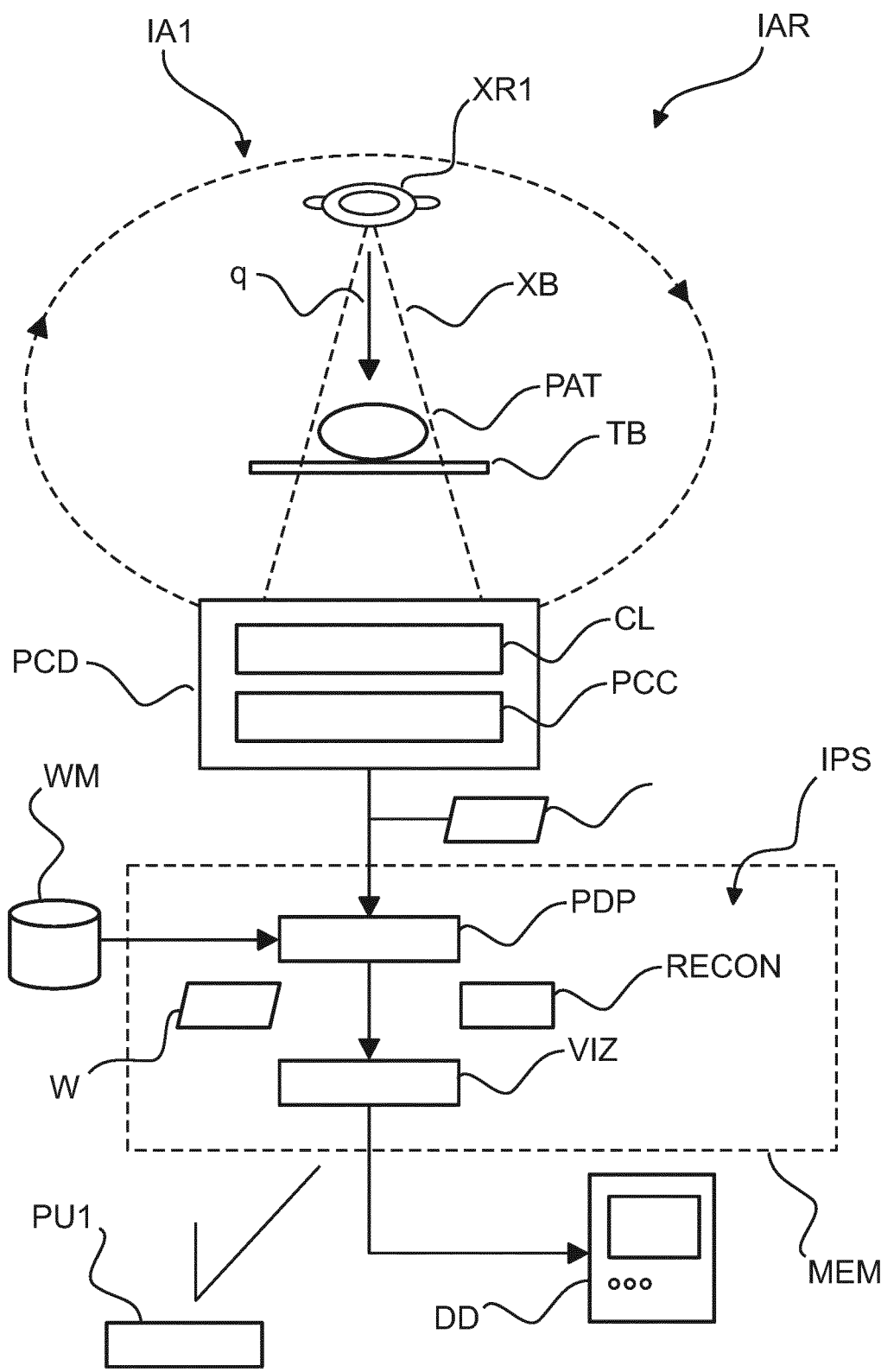
FIG. 1 shows a schematic block diagram of an imaging arrangement using a photon counting detector.

With reference to FIG. 1, this shows a schematic block diagram of an imaging arrangement IAR envisaged herein in embodiments.

The imaging arrangement IAR includes an X-ray imaging apparatus IA1 configured for spectral imaging. More particularly, the spectral imaging capability is detector based. Yet more specifically, the imager IA1 includes a photon counting detector PCD. Broadly, the photon counting detector PCD allows acquiring projection data at different energy levels. Specifically, as explained in more detail below, the projection data includes count data produced by the photon counting detector PCD. The count data may be processed into a number of different image types to better assist diagnosis as compared to traditional energy integrating based detectors. In particular, monochromatic imagery, material specific maps for better soft tissue discrimination may be obtained, including material decomposition.

In addition, the projection count data may also be processed by the IPS into energy integrated imagery similar to that obtainable by a conventional energy integrating detectors.

Broadly, the imaging arrangement IAR includes an image processing system IPS including in particular a projection data processor PDP that is configured to apply specially configured weights w to the count projection data it received from the photon counting detector PCD. Applying the weights allows the projection data processor PDP "emulate" at high fidelity a given energy integrating detector of another imaging apparatus. In other words, the projection data processor PDP, allows better cross modal comparison of photon counting detectors PCD based imagery with energy integrated detector based imagery. The imagery processed by the proposed projection data processor PDP has the "look and feel" of more conventional imagery obtain by an energy integrating detector. The proposed system IPS may be of particular benefit to medical or research sites that maintain both, photon counting detectors and energy integrating detectors. In addition, because of the high fidelity emulation of energy integrating detector based imagery, the proposed PDP is more efficient as it may allow dispensing with conventional energy integrating detectors altogether.

Components of the image processing system IPS including the projection data processor may be arranged as software modules that are run on a single or plural computing unit PU. The computing processing unit may be a general purpose and arranged remotely from the X-ray imaging apparatus IA1. In particular, the image processing system may be arranged remote and outside a housing of the detector PCD. The computing unit PU may be suitably interfaced to receive the projection count data $\pi$ produced by the photon counting detector through a suitable wired or wireless communication network. Some or all of the image processing system components may be held in single, centralized memory MEM and executed by the one or more processing computing unit PU. In the alternative, the image processing system IPS may be held such that the components are distributed across a plurality of memories MEM in a computing environment across multiple computing systems, logically or geographically distributed. Alternatively, some or all of the components of the image processing system may be arranged in hardware such as in suitably programmed FPGA's or ASCIS or others. In embodiment, rather than arranging the image processing system outside of the housing detector PCD and remote therefrom, some or all of the components may be instead integrated into the detector PCD itself as an on-board post processing stage.

Before explaining the components of the image processing system IPS more fully, the X-ray imaging apparatus IA1, including the photon counting detector PCD, is first discussed in more detail.

The photon counting detector is arranged opposite an X-ray source XR1 to thereby define a portion of space between the two, referred to herein as the examination region. The patient or object to be imaged, or at least a region of interest (ROI) thereof, resides in the examination region during imaging. Specifically, the X-ray source generates in general polychromatic X-radiation in form of an X-ray beam XB. The X-ray beam emanates from the X-ray source XR1 during use. Specifically, the X-ray beam traverses the examination region, and hence the ROI, and then propagates along main direction q towards the photon counting detector PCD to be registered there. The X-beam, after traversal of the object or patient, emerges at the far side in modified form due to interaction with tissue or material in the ROI. The modification experienced by the beam encodes information of the internal structure of the ROI and it is this information that one wishes to visualize. During imaging, the patient or object to be imaged may rest on an examination table TB or other support, although this is not required in all embodiments, as the patient may be standing in some embodiments during imaging.

The X-ray imaging apparatus IA1 is specifically envisaged in embodiments for tomographic imaging to implement spectral photon counting computed tomography (SPCCT). The imaging apparatus may be arranged as a C- or U-arm imager or as CT scanner with a gantry having a bore in which the patient lies during imaging. Although tomographic imaging is mainly envisaged herein planar projection based radiography systems are also envisaged in alternative embodiments.

Turning now in more detail to the tomographic embodiments, the X-ray source rotates on an imaging orbit around the patient during imaging, not necessary in a full revolution. In embodiments, the detector DCP rotates with the source XR1 and acquires projection count imagery it from different directions q. Co-rotation of the X-ray detector with the X-ray source is not required in all embodiments however, such as in a $4^{th}$ generation CT scanner. CT scanners of all generations, $1^{st}$ through $4^{th}$, are envisaged herein, with scanner or the $3^{rd}$ generation being the preferred embodiment.

The X-ray beam, having an initial spectrum intensity upon egressing the X-ray source, interacts, as mentioned above, with tissue material in the patient and emerges at the far end of the patient as the modified beam. As a result of the tissue interaction the modified beam has as changed spectrum as compared to the initial spectrum. This post-interaction beam is then registered at the photon counting detector PCD for each projection direction q.

Turing now in more detail to the operation of the image processing system IPS, the projection count data it as acquired from different directions q are output at a detector interface and forwarded to the image processing system IPS. The specially configured weights configured to emulate energy integrating behavior are held locally or remotely on a weight data base WM. The weight data, to be described more fully below, may be generically referred to herein as "w", with the understanding that the weight data in general comprises a plurality of numbers, in particular one or more sets of numbers. The projection data processor PDP accesses the weights w and applies same to the count projection data, preferably for each direction q.

The so weighted projection count data may then be passed to a reconstructor module RECON that implements a tomographic reconstruction algorithm to produce axial cross sectional image data. The axial cross sectional image data may represent internal structure in a plane through the imaged patient or object. In other words, the projection data, with weights applied, is mapped by the reconstruction module RECON from the projection domain to image domain. Image domain includes respective planes in the examination region that intersect the patient. The projection domain is located at detector PCD. The above described procedure may be repeated for different image domain planes along a longitudinal axis Z of the patient to obtain a plurality of cross sectional image data at respective, different positions z on axis Z. The cross sectional imagery forms a 3D image volume. The different sets for projection data for different z positions may be acquired by moving the source and/or the support TB (on which the patient rests) along axis Z during the imaging. This longitudinal motion may be achieved for example by using a helical X-ray scanner.

The image data as produced by the re-constructor at its output may be passed on to a visualizer VIZ. The visualizer maps the image data to certain image values in a range such as the Hounsfield Unit (HU) scale, or other suitable imaging scales. The so mapped image values may then be mapped to color or grey values and may then be visualized on a display device DD as cross sectional imagery. Users such as medical personnel can then view the imagery for diagnostic or other purposes.

Before explaining the operation of the projection data processor PDP and how the specially configured weights w for energy integration emulation are gotten, the photon counting detector PCD will be explained in more detail.

The photon counting detector PCD as envisaged herein in embodiments includes a conversion layer CL and, communicatively coupled thereto, photon counting circuitry PCC. Broadly, the conversion layer CL converts incident photons in the X-ray-radiation into electrical signals, in particular pulses. The electrical pulses are then processed by the photon counting circuitry PCC into count data based on pulse height. The height is proportional to the energy of an individual photon that caused that pulse when interacting in the conversion layer. These pulses are then processed against a plurality of energy thresholds to so categorize the detected electrical pulses according to their energy. Two, three, four, five or more such energy thresholds may be used. The projection count data measures, for each energy interval, sometimes referred to as a "bin", photon flux, the number of photons per unit time in that bin recorded during the acquisition. Recordal of such count data in the multiple bins is done for each projection direction q.

Turning now in more detail to the conversion layer CL, this may be arranged as a direct conversion layer or an indirect conversion layer. Preferably a direct conversion layer is used. In embodiments the direct conversion layer is arranged as a semi-conductor (e.g. CZT, CdTe or Silicon or others) or other crystalline layer. The conversion layer is preferably structured into a plurality of detector pixels PX. Electrical pulses produced by each pixel PX are then processed by the photon counting circuitry PCC as described above. In embodiments, each individual detector pixel is coupled through a communication line with the photon counting circuitry to so communicate the electrical pulses thereto.

Figure 2:
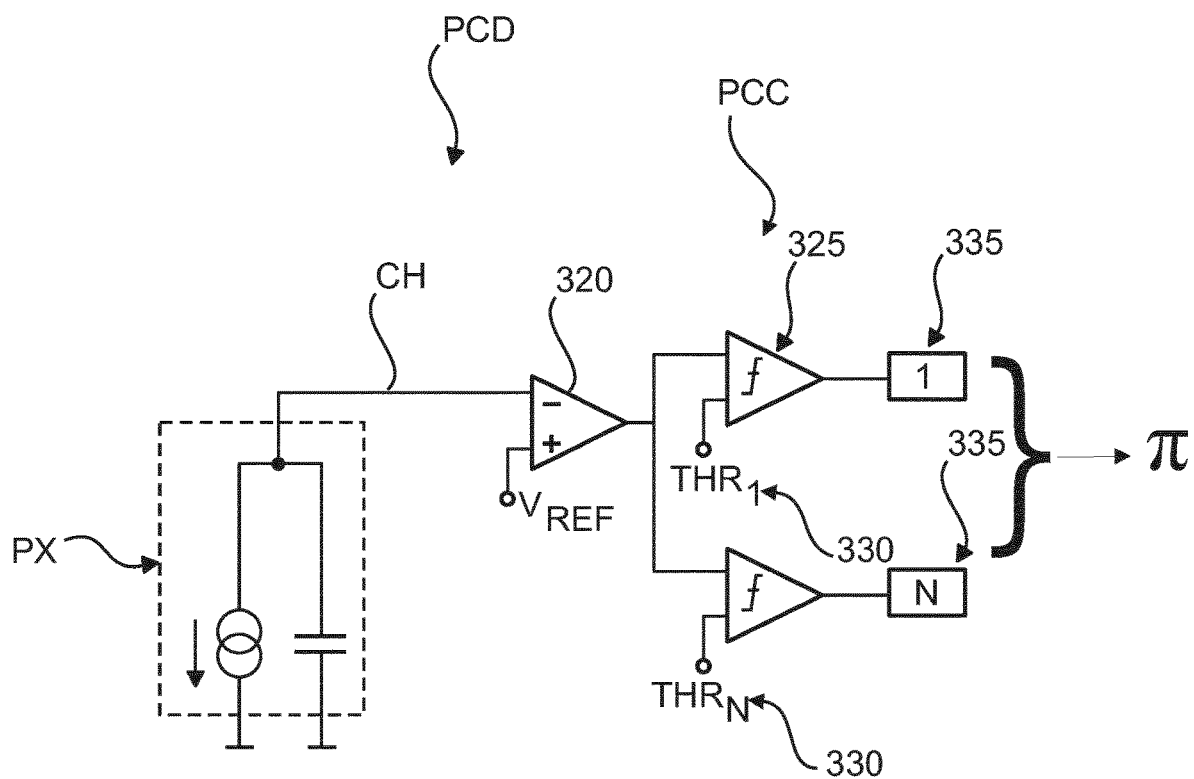
FIG. 2 shows a schematic diagram of photo counting circuitry coupled to a detector pixel.

Reference is now made to FIG. 2 that shows in a schematic fashion the photon counting circuitry PCC in more detail and according to one embodiment. Only a part of the photon counting circuitry PCC is shown in association with a single detector pixel PX. It will be understood that similar circuitry is used for each of the other detector pixels. In alternative embodiments not each detector pixel may have its own photon counting circuitry, as the photon counting circuitry may be switchable among a plurality of such detector pixels. Preferably, however, each pixel PX has its own photon counting circuitry portion as indicated in the Figure.

In yet more detail, exemplary pixel PX produces electrical pulses as described above. A pulse has a magnitude ("height") corresponding largely to the energy of an impacting photon. The higher the photon's energy, the higher the pulse magnitude that can be detected at the respective pixel PX. Each pixel electrode is coupled by an individual signal line (or "(pixel) readout channel") CH with photon counting circuitry, shown to the right of FIG. 2.

According to one embodiment, the electrical pulses generated at the pixel PX is processed by the photon counting circuitry PCC in the following manner:

Optional conditioning circuitry includes a pre-amplifier 320 that amplifies each electrical signal generated by respective pixel PX.

The optional conditioning circuitry may further include a pulse shaper (not shown) to processes the amplified electrical signal for a detected photon and to generate a corresponding analog signal that includes the pulse height such as a voltage/current or other pulse indicative of the detected photon. The so generated pulse has a predefined shape or profile. In this example, the pulse has peak amplitude that is indicative of the energy of the detected photon.

An energy-discriminator 325 energy-discriminates the analog pulse. In this example, the energy discriminator 325 includes a plurality of comparators 330 that respectively compare the amplitude of the analog signal with a respective threshold that corresponds to a particular energy level. Neighboring threshold define an energy bin. Said differently, discriminator 325 operates to determine "height" of the incoming pulses as generated by shaper. More specifically, each comparator 330 produces an output count signal that is indicative of whether the amplitude of the pulse exceeds its threshold. In this example, the output signal from each comparator produces a digital signal that includes a transition from low to high (or high to low) when the pulse amplitude increases and crosses its threshold, and from high to low (or low to high) when the pulse amplitude decreases and crosses its threshold.

In an exemplary comparator embodiment, the output of each comparator transitions from low to high when the amplitude increases and crosses its threshold and from high to low when the pulse amplitude decreases and crosses its threshold.

A counter 335 counts the rising (or in some embodiments the falling) edges respectively for each threshold. The counter 335 may include a single counter or individual sub-counters for each threshold. Optionally, in case of two-sided bins only, there is a 2-sided-energy binner (not shown) that energy-bins or assigns the counts into energy ranges corresponding to ranges between the energy thresholds. In fact, in the preferred embodiment with high flux, there is no two-sided binning operation into ranges but it is purely the counts of threshold crossings (i.e., one-sided binning) that are being registered. Count data for one-sided bins may however be transformed in to two-sided bin data by taking differences between data in neighboring bins as will be illustrated below for embodiments.

The photon counting circuitry furnishes at its output, for each pixel PX, a number of counts in each bin as recorded in unit time. The projection (photon) count data π includes the photon count rates per bins and pixels. For each pixel, the photon count data is a vector $C^i=(c_1, \ldots c_K)^i$ of count rates $c_k$ for each bin, whilst i denotes the respective pixel and $1 \le k \le K$ the number of energy bins used. Exemplary values for K are 3, 5 or other. In rotational systems such CT or C-arm, the recorded count rates may be different for different projection directions q so the above notion may be supplemented with an additional index for the projection direction. In this later case, C forms a (count data) sinogram in the CT embodiment. There may be further index for the respective position z on imaging axis Z.

Figure 3:
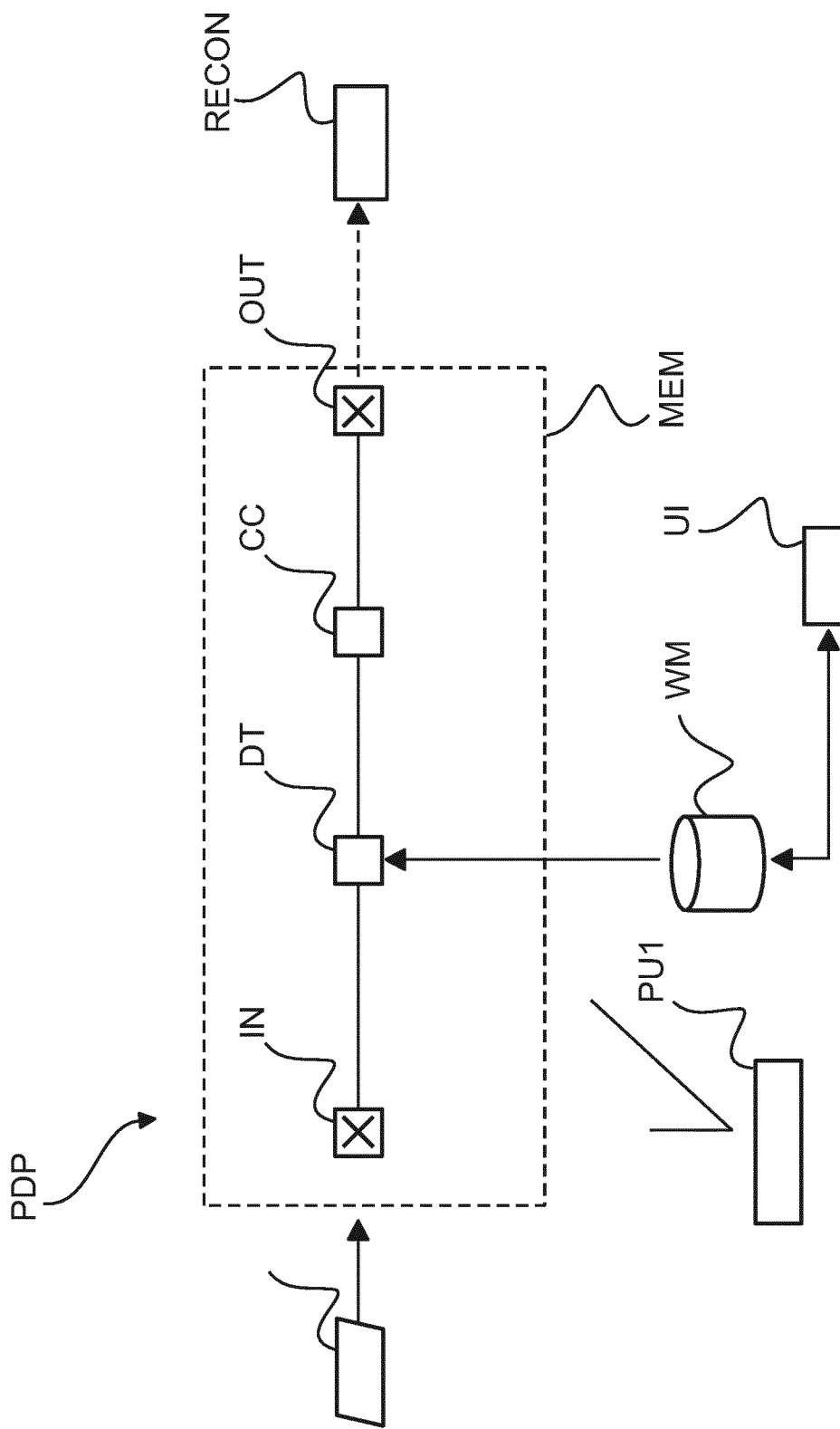
FIG. 3 shows a diagrammatic block diagram of a component of an image processing system configured to process count data produced by a photon counting detector.

The so quantized projection count data $C^i$ may then be processed by the image processor IPS. This will now be explained in more detail, with reference to FIG. 3 which shows a block diagram of the projection data processor PDP.

The projection data processor PDP receives the projection count data π produced by the photon counting circuitry PCC of the photon counting detector PCD. Components of the projection data processor PDP include a conversion component CC.

The conversion component CC allows converting the count data it to projection data that approximates or resembles line integral (intensity) values usually registerable by an energy integrating detector.

Operation of the conversion component CC is based on calibration data held in a memory. This calibration data may be referred to herein as count-to-path-length (C2PL) calibration data. In more detail, during the calibration procedure, referred to herein as the C2PL-calibration to distinguish from another type of calibration discussed below in particular at FIG. 8, certain configurations of calibration materials are placed in the X-ray beam XB of the imager IA1. Suitable materials ("phantoms") are any one of water, polymer(s) such as Delrin® or Teflon, or metals such as Tin, Aluminum, K-edge materials (such as AU, Bi, Pb), or others. The material should have at least two different thicknesses. One exposure may then be enough, or otherwise multiple items of said material are stacked up to realize different thicknesses and two more exposures may need to be run as reported for instance by R Alvarez in "*Estimator for photon counting energy selective X-ray imaging with multi-bin pulse height analysis*", publ. in Med. Phys. 38 (5), May 2011. In practice, a large number of different material thicknesses are realized because the relationship between path length and photon flux is non-linear due to the effect of pulse pile-up, see for instance "*Radiation Detection and Measurement*", Glenn F. Knoll, John Wiley & Sons; 4th edition (24 Sep. 2010)).

The calibration operation results in pairs of data points data points (c, $l_{calib}$). That is, each known path length $l_{calib}$ (the phantom thickness) is associated with the count data c as measured in the phantom calibration procedure.

Operation of the conversion component CC according to one embodiment may now be explained in more detail, assuming the calibration data (c, $l_{calib}$) is known and held in memory. It may be convenient to express the count rates c in logarithmized form as log-counts $\overline{logc}$. The conversion component CC is configured to compute the path length l that "best" explains the given photon counts as measured for the different energy bins per pixel. Computation of the best path length l may be implemented by formulating a minimization problem in terms of a cost function that quantifies the goodness of how well the length is to explain the count rates. A cost function envisaged in embodiments is based on a least square approach, in particular a weighted least square (WLS) approach. In WLS, the "weights" are not related to the emulator weights to be discussed later. In the WLS approach a covariance matrix with cross error terms is used. Applying WLS for present purposes, the optimization may be formulated in embodiments as:

$$l_{min} = \min_{l}(\overrightarrow{\log c} - \overrightarrow{\log c}_{calib}(l))^T COV^{-1}(\overrightarrow{\log c} - \overrightarrow{\log c}_{calib}(l)) \quad (1)$$

with $COV^{-1}$ being the inverse of covariance matrix COV of the photon counts $C = \vec{c}$ for each pixel and projection for one specific measured path length l. Each off-diagonal entry i,j in COV represents a correlation between counts in bins i,j, with diagonal entries representing the respective statistical variances for each bin. If a two-sided bin counter is used, the off-diagonal entries are zero (in the absence of pulse pile-up). The number of rows and columns in COV, and hence in $COV^{-1}$, equal the number or bins.

The calibration data $\overrightarrow{\log c}_{calib}$ is only known at the path length $l_{calib}$. For minimizing (1), the counts $\log \vec{c}_{calib}(l)$ need to be known at all path lengths l. Linear or cubic spline interpolation can be used to calculate $\overrightarrow{\log c}_{calib}(l)$ from the known data points $\overrightarrow{\log c}_{calib}(l_{calib})$. By this, even in regions with strong pile-up the right (e.g., water) equivalent path length can be estimated. The calibration data C2PL may be arranged and stored in a look-up table (LUT).

The phantom based C2PL calibration is intended to replace the air normalization, water beam hardening correction, channel correction and Hounsfield correction currently applied in conventional CT preprocessing chain. It will be understood that the WLS approach is but one exemplary embodiment to solve the C2PL problem. Other cost functions may also be used. Also, the minimization problem may be recast into a dual formulation as a maximization problem to maximize a utility function. Solving (1) does not necessarily yield a global minimum but a local minimum. If the optimization problem for the C2PL calibration is solved by iteration, a stopping condition may be defined.

The conversion component allows operating the photon counting imager IA1 in "conventional mode", that is, as if it was an imager with a conventional energy integrating imager.

However, it has been observed by Applicant that merely applying this count data-to-path-length conversion may not faithfully emulate an energy integrating detector. For instance, Applicants have found that locally there may be deviations of up to 30% in HU units between an image reconstructed from count data via path length conversion, and a corresponding image for the same object but obtained by using an energy integrating detector. This deviation may be confusing for clinical personnel.

In order to be able to generate more faithful energy integrated imagery, the projection data processor PDP includes, in addition to the conversion component CC, a further component referred to herein as the count data transformer DT. Operation of the count data transformer DT is based on the weights w mentioned above, referred to herein as the emulator weights w.

The count data transformer DT operates to apply the emulator weights to the projection count data it as received at input port IN from the photon counting detector. Preferably, the weights are so applied before processing by the data transformer DT. Application of the weights to the projection count data may be done in a multiplicative fashion on the one-sided or preferable on the two-sided bin data. However, this may not exclude other modes of application, for instance, the weight may be additively applied or by using more involved functional expression $F(\pi,w)$. F may be referred to herein as the weight-application operator. In a preferred embodiment, a simple multiplicative application is used where respective weights w are multiplied with the count data for each pixel and, if applicable, for each imaging direction $_q$ and/or z position. The weights w may comprise one or more sets of numbers. Each set may be stored and processed as a vector $w^i = (w_1^i, \ldots w_K^i)$, with the length K of each such "weight vector" equaling the number of bins. The weight vectors may depend on pixel i. A respective weight vector $w^i$ is applied to a respective count vector $C^i$ for a given pixel position i by multiplying each count $c_k$ in each bin by a respective weight $w_k^i$. Alternatively, and in embodiments, the same weight vector may be used for all pixels i, so there is no pixel dependency of the weight vector. The same one or more weight vector may be used for all the projection data, or there may be a further dependency on the scan direction q.

Preferably, before applying the weights to the count data $\pi$, and if the photon counting circuitry PCC does not use two sided bin already, the counting data as per one-sided (OS) bins may need to be transformed first into two-sided-bin (TS) data before applying the weights. Exactly how the weights are gotten will be explained in more detail below.

Explaining now in more detail operation of the count data transformer DT, this component operates to modify the counts $\vec{c}$ by applying the emulator weights $w\vec{w}$ to emulate with high fidelity an energy integrating detector. The mentioned optional bin-transformation one-sided counts need into two sided counts may be implemented as:

$$c^{TS}(\text{bin}) = c^{OS}(\text{bin} + 1) - c^{OS}(\text{bin}) \quad (2a)$$

$$c^{TS}(\text{bin}_{max}) = c^{OS}(\text{bin}_{max}) \quad (2b)$$

Then the weights may then be applied, for instance multiplicatively, per bin as:

$$c_w^{TS}(\text{bin}) = c^{TS}(\text{bin}) * w(\text{bin}) \quad (3)$$

Optionally, the weighted counts are transferred back to one-sided bins, are then fed into the conversion component CC needed to calculate the material (e.g., water) path length. The same weights w as used by the data transformer DT for the scan projection data it are also applied to the count data c in the C2PL calibration data. This ensures the count data in the C2LP calibration data and in the scan projection data $\pi$ are consistent and comparable after the transformation by data transformer DT.

For a detector with 3 energy bins, and weight vector $w=(w_1, w_2, w_3)$ the two-sided-to-one-sided-bin count transformation may be compactly written and implemented by matrix operations as:

$$\tilde{c}_w^{OS} = \begin{pmatrix} 1 & 1 & 1 \\ 0 & 1 & 1 \\ 0 & 0 & 1 \end{pmatrix} * \begin{pmatrix} w_1 & 0 & 0 \\ 0 & w_2 & 0 \\ 0 & 0 & w_3 \end{pmatrix} \tilde{c}^{TS} \quad (4)$$

The emulator weights may in general differ or each pixel position. However, in the preferred embodiments constant weights are used for some or all pixels and acquisition direction q and/or z position. An array structure is used to store respective emulator weights for each given pixel position. The weights may also be further differentiated according to acquisition direction q and z position, in which case a higher dimensional matrix structure may be used to store the weights in association with pixel position and any one or more of acquisition projection direction q and z position.

To sum up operation of the projection data processor, in use, after acquisition of the projection count data it, this is received at input port IN and passed on to the count data transformer DT. The emulator weights may be retrieved from weight memory WM. The count data transformer DT transforms the data into transformed weighted count data based on the retrieved emulator weights. The so transformed count data is then mapped by the conversion component CC onto path length data using the C2PL calibration data (which was also transformed into weighted count calibration data) held in a calibration memory (not shown). The C2PL data may be held together with the emulator weights in a single memory or the two data sets may be held in different memories.

The PDP outputs at output interface OUT, for each pixel and, if applicable, for per projection direction q and/or position z, a corresponding approximate path length. This path length data provided at output interface OUT may then be used by reconstructor RECON to reconstruct a HU-image in image domain. This reconstructed image may be considered an emulation of image reconstructable from data acquired by an energy integrating detector. The emulated image may be mapped on a suitable color or grey value scheme by the visualizer. The associated image color or grey values are then rendered by video circuitry as a visualization onto on the display device DD.

The proposed system IPS may further include a user interface UI, that allows the user to interactively change the stored weights previously computed in an automatic optimization scheme as will be explained in more detail below. The user interface such as a graphical user interface including suitable input widgets such as sliders allows the user to change the value of individual weights either pixel wise or in sub-groups. The user interface UI may be communicatively coupled to the reconstructor RECON. Each change to the weights requested by the user triggers re-reconstruction by the re-constructor and this can be done until the user is satisfied that the imagery now looks as if it had been obtained from an energy integrating detector.

Figure 4:
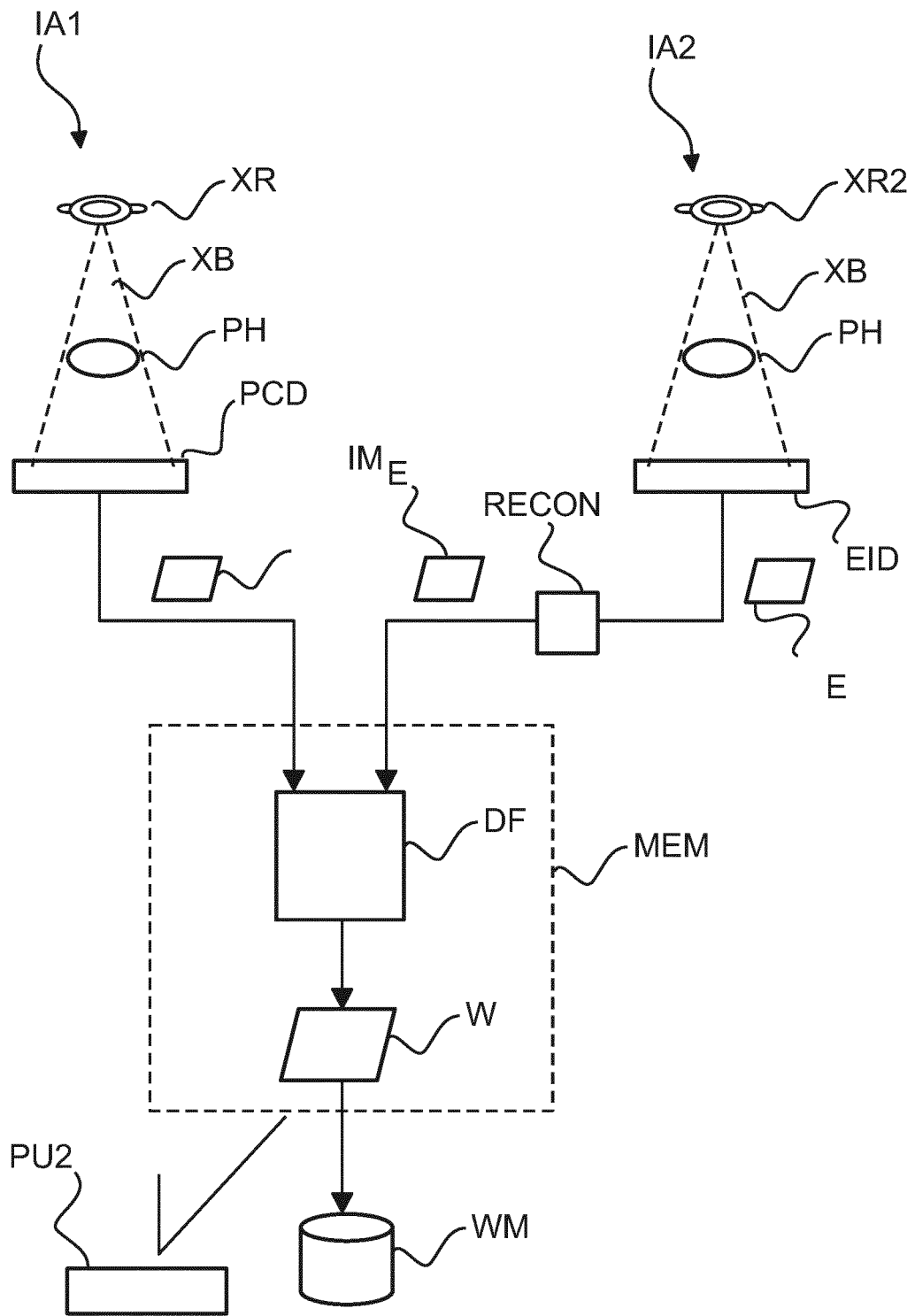
FIG. 4 shows an arrangement to compute weights based on test imagery or data received from the photon counting detector and an energy integrating detector.

Reference is now made to FIG. 4 which shows a block diagram of a computerized system configured to obtain the above described emulator weights W. The described setting uses an existing imaging apparatus IA2, having an energy integrating detector EID, in conjunction with the photon counting imager IA1 described above. The system allows tuning output of the photon counting detector PCD to imaging properties of the existing energy integrating detector EID.

An experimental procedure based on this system may be performed as follows. A phantom PH is placed into the examination region of the conventional imaging apparatus IA2. Its X-ray source XR2 is then operated to generate a beam that transverses the phantom and causes the energy integrated detector EID to detect conventional, energy integrated, projection data $\pi_E$. The energy integrated projection data $\pi_E$, includes per pixel intensity measurements, line integrals, that each represent relate to integrated energy deposited by incident photons of different energies, after passage through the phantom PH. The phantom PH is a test object, preferably made from one or plural materials such as water.

If a tomographic setting is envisaged, the X-ray source XR2 will rotate, as described above in relation to the photon counting imager IA1, around the phantom object PH a rotational orbit, whilst the detector EID collects projection data $\pi_E$ from different directions. The conventional projection data $\pi_E$ as collected by the energy integrated detector EID is then processed by reconstructor RECON to obtain one or more cross sectional image data $IM_E$ associated with the conventional energy integrating detector AI2. This image data may $IM_E$ may be called, for present purposes, an energy-integrated test or target image $IM_E$ or calibration image. The calibration image IME may be acquired at a relatively high X-ray dose to reduce image noise. In this connection, "high" is understood to mean a higher dose than one would be using for imaging a patient.

The same or a similar phantom is then imaged in a manner described above by the spectral imager IA1 having the photon counting detector PCD to obtain as described above the projection count data $\pi$, referred to herein now as $\pi_C$.

The calibration image IME and the count data $\pi_C$ is then forwarded to a data fitter DF as input. The data fitter DF computes the emulator weights, based on the input. In embodiment, the data fitter may implement an iterative optimization algorithm to adjust an initial set of weights $w_0$ so that imagery re-constructible from the count data $\pi_C$, after conversion into path length, corresponds to the test image $IM_E$. The conversion may be accomplished by the data fitter DF using a component similar to the conversion component CC discussed above in relation to the projection data processor PDP.

The correspondence or match between the two images, the image reconstructed from $\pi_C$ and the test image $IM_E$, can be quantified by a suitable similarity measure $\mu$, such as mean-square-root distance or by at least squares-function, or by using any other suitable similarity measure, such as an $L^P$ norm, with p other than ½. The measure $\mu$ may be evaluated in the whole image or just in one or more ROIs and may be formulated as an objective function F, depending on $w_0$. The adjustments of the initial set of weights $w_0$ may be accomplished by an iterative optimization scheme such as Newton-Raphson, conjugate gradients, Nelder-Mead, or any other. The optimization algorithm is configured to adjust, in one or more iteration cycles, the initial set of weights so that the objective function is minimized. It will be understood that optimization does not necessarily yield a global minimum but may return instead an approximation of a local minimum which may however be sufficient for most purposes. A stopping condition may be defined in terms of a pre-defined threshold. The weights are adjusted until the objective function returns a value below the pre-defined threshold. Once the stopping condition is met, the current set of weights are then output by the data fitter DF as output. The so output set of weights are the emulator weights. The emulator weights may be stored in weight memory WM.

Instead of using the above described experimental approach based on real measurements, it may also be possible to compute the weights theoretical through modeling and simulation. In embodiments this can be done by computing spectra or more specific count data of the two detectors PCD and EID based on respective detector specifications, the initial spectra and material properties of the phantom. The detector specifications may include the detector absorption efficiency. The phantom material properties may include Z-atomic number(s), material density, etc. The initial spectra may be computed from specifications of the X-ray source, including cathode current, tube voltage and anode material. An approximation of the output spectra in response to exposure for both detectors may then be computed through running a Monte-Carlo simulation for instance, where scatter and absorption events can be accounted for through suitable models for the respective cross sections as otherwise known, such as the Klein-Nishina model for the scatter cross-section, whilst the photoelectric absorption cross section may be modelled by the familiar $Z/E^3$ law. The Monte Carlo (MC) simulation may be implemented using the probabilistic Metropolis-Rosenbluth-Teller algorithm, described by N Metropolis et al, in "*Equation of State Calculations by Fast Computing Machines*", J. Chem. Phys. 21, p. 1087, 1953. Other implementations and/or non-MC simulations are also envisaged.

Figure 5:
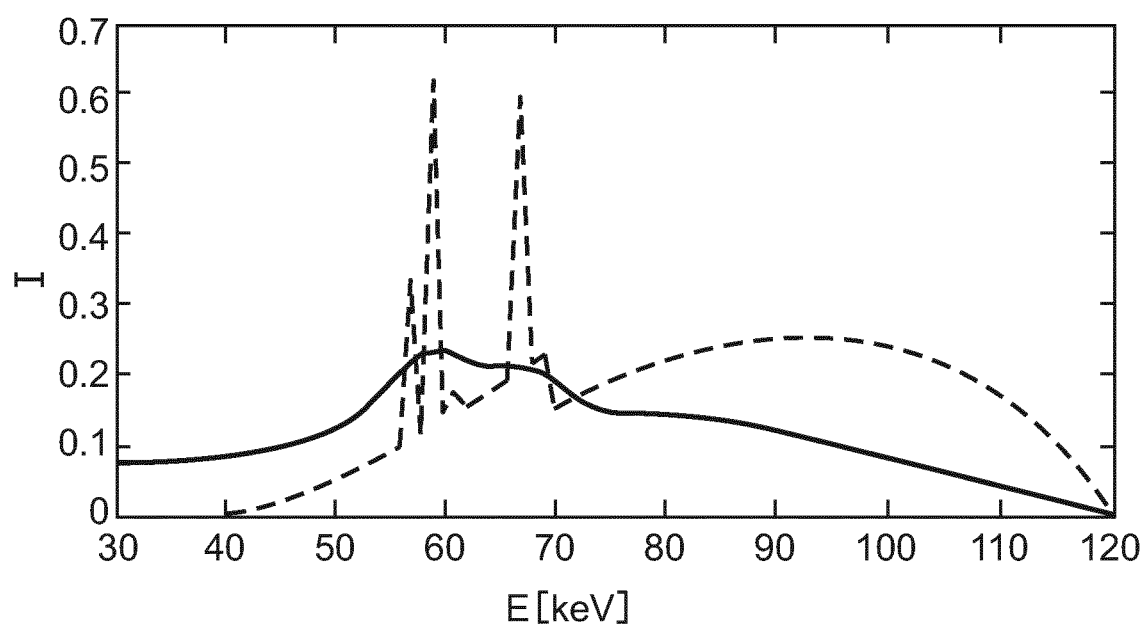
FIG. 5 shows exemplary spectrum data in relation to a photon counting detector and an energy integrating detector.

Exemplary spectra, intensity versus energy curves, for both detectors, obtainable through a computation as outlined above, are shown in FIG. 5. Specifically, the spectrum of a photon counting (including the spectral response function) and a spectrum for an energy integrating detector are illustrated for an attenuation by 40 cm of water. The curve with the two sharp peaks is the spectrum of the energy integrating detector.

Figure 6:
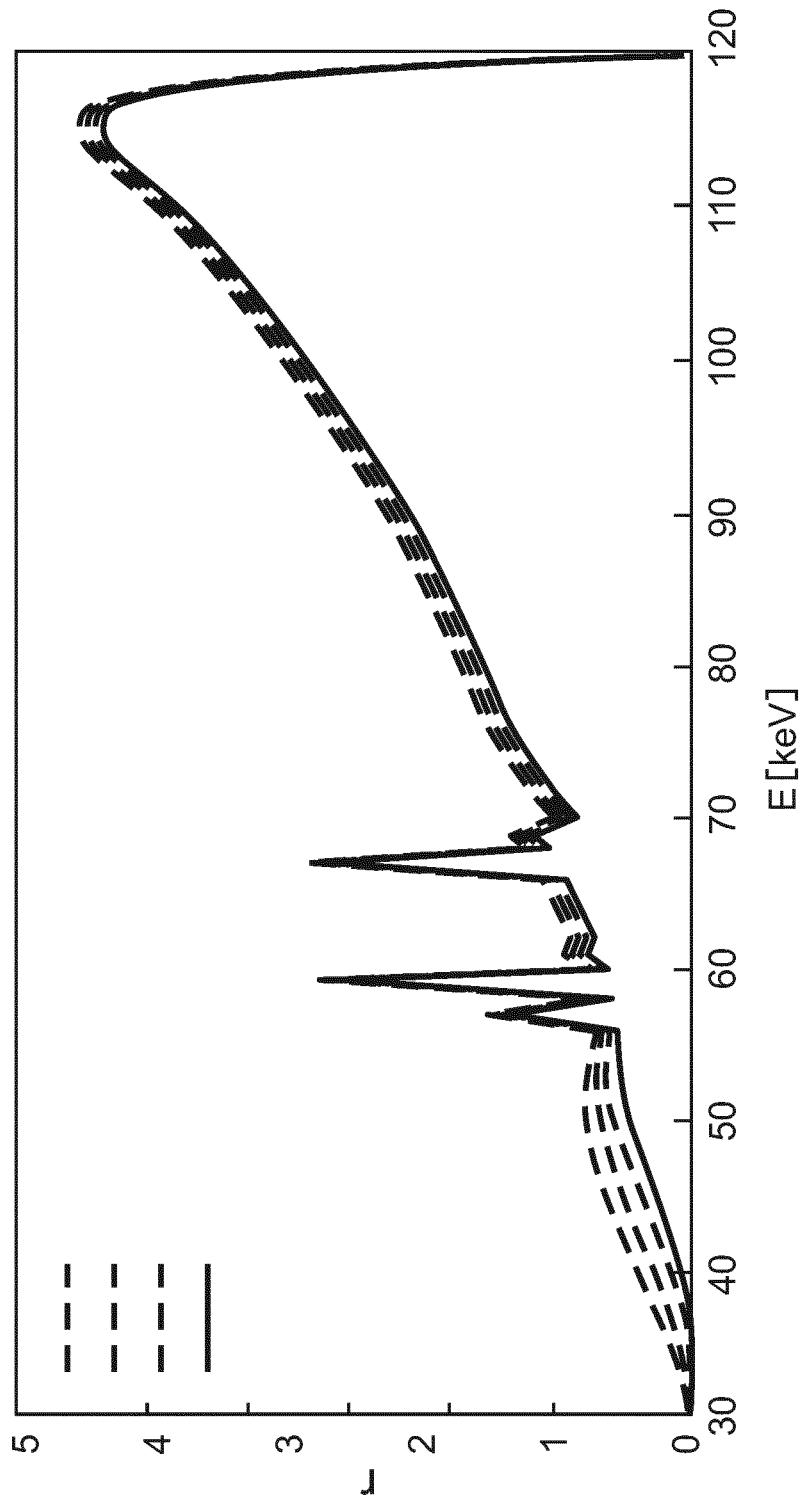
FIG. 6 shows exemplary ratios versus energy obtained from the exemplary spectra in FIG. 5.

From the so computed spectra, ratios r may be obtained per energy as shown in the exemplary ratio curve of FIG. 6. Interestingly, the ratio curves do not have a strong dependency on phantom thickness. FIGS. 6 shows four such exemplary curves, for (from top) water thicknesses 10, 20, 30 and 40cm. It is therefore possible to perform the simulation for a given phantom of fixed thickness, such as 40 cm. The ratios r may be formed as $r(E)=Ie/Ip$ for each energy value E, with $I_e$ being the intensity as per energy interval for the energy integrating detector and $I_p$ being the intensity as per energy interval for the photon counting detector. The emulator weights may then be derived as averages $\bar{r}$ over the $r(E)$'s. Specifically, the counted data in a given bin i for a given energy range ERN, may be weighted by multiplying count rate in bin i by an average ratio $\bar{r}$. The average ratio may be obtained by forming an average from ratios $r(E)$ for all energy values E in the given range ERN as captured by bin i. In other words, the emulated weights are averages for the obtained ratio curve for energies included in the energy ranged for a given one of the bins.

Figure 7:
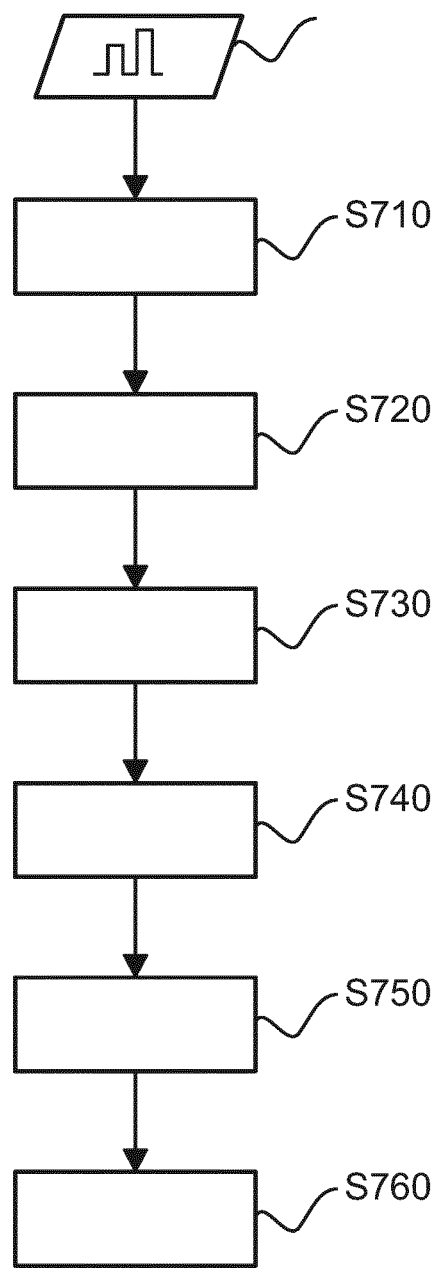
FIG. 7 shows a flow chart of an image processing method.

Reference is now made to FIG. 7, which shows a flow chart of an image processing method as envisaged herein in embodiments. The steps of the method to be described in the following may be used to implement the above systems in FIGS. 1-4 but the below described steps may also be understood to be a teaching in their own right, not necessarily tied to the architecture of the systems discussed in FIGS. 1-4.

At step S710 energy resolved count data is received generated by a photon generating detector PCD. Preferably, the photon counting detector has at least two image bins, but preferably has more than two such as three, four, five or even more.

In step S720 the count data is transformed into transformed count data. The transformation is implemented by applying one or more weights to the count data. The weights have been previously obtained based on i) data for the photon counting detector or a different photon counting detector and, in addition, ii) on data in relation to an energy integrating detector. The data for the photon counting detector may include projection count data acquired during imaging a test object, such as phantom comprising one or more suitable materials such as any or more of water, aluminum, Derwent etc. In embodiments, the data may be computed through simulation from detector specifications, X-ray source specifications and material properties of a virtual test body. The data in relation to the energy integrating detector may include projection data acquired during imaging of a test body phantom, or, preferably, a test image reconstructed from such projection data. Any reconstruction algorithm may be used for this such, as FBP or iterative reconstruction, algebraic reconstruction or other.

The energy integrating detector may also be referred to as the target as it is imaging properties of this energy integrating detector one wishes to emulate by applying the weights.

At step S730 the so transformed count data is then converted into material path length data. The path length data refers to a conceptual thickness of a reference material such as water or water equivalent or other material of similar radiodensity. In this manner, each count data for each pixel is associated with a respective path length. The proposition is, that, for a given pixel position, had the material of the assigned thickness been exposed to the X-radiation used to when acquiring the count data, one would have observed approximately the same counts as received at step S710 for that pixel. The path length data may be further converted into line integrals or other attenuation coefficient based scale.

At step S740 the obtained through material path length data or line integral data is then reconstructed to image data in a known manner using any reconstruction algorithm. The image data may be mapped to HU values. The image data is so obtained is considered an emulation of imagery obtainable by the real or virtual energy integrating detector that was involved when computing the weights. Preferably, the reconstruction algorithm used in step S740 is the same as the one used when computing the weights, on which more further below at FIG. 8.

At step S750, which is optional, the so reconstructed image data is then output, such as displayed on a display device, stored in a memory or otherwise processed.

In optional step S760 the applied weights may be changed in response to a user request. In this case the changed weights are re-applied and the above described method steps are repeated from step S730 onwards to produce a new image at step S740 which is preferably displayed in step S760. In this manner the user can use trial and error to tweak the weights so as to achieve an image that according to the user's opinion looks like one would have obtained had an energy integrating detector been used.

Figure 8:
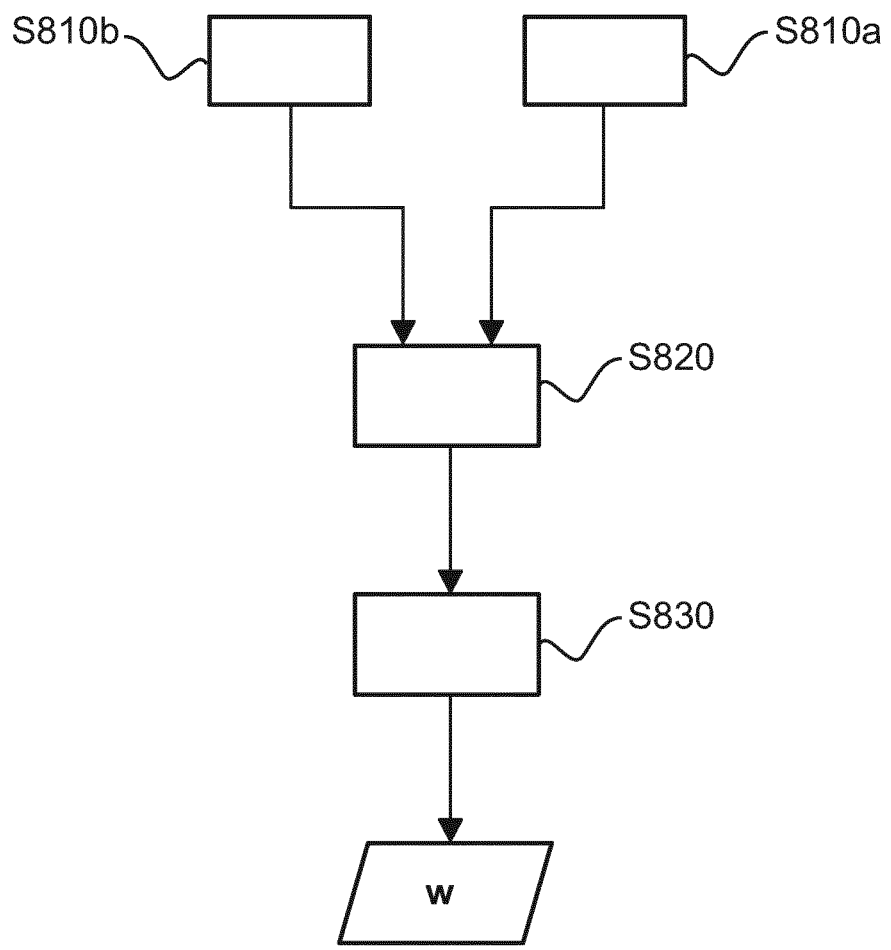
FIG. 8 shows a flow chart of a calibration method.

Reference is now made to the flow chart of FIG. 8 which shows a method of calibration. In particular, the calibration method described in the following may be used to compute the emulator weights as used in the method of FIG. 7.

In step S810A, energy resolved calibration data from the photon counter detector is received.

At step S810B, calibration image data for an energy integrating detector is received.

At step S820 a data fitting operation is performed by adjusting an initial set of weights to be applied to the energy resolved data so that image data $IM_p$ re-constructible from the so weighted data corresponds to the calibration image data $IM_e$ for the energy integrating detector.

An automatic optimization scheme may be used based on a suitable objective function that quantifies the difference between the two reconstructed images $IM_p$, $IM_e$. The emulator weights are then obtained by adjusting, in one or more iterations, the initial weights so as to minimize the objective function f, as function of the weights, until a stopping condition is satisfied. This optimization problem may be formally written as:

$$f^w = \mu[R(cc(F(\pi_p, w)), R(\pi_e)] \quad (5)$$

$$\operatorname{argmin}_w f^w \quad (6)$$

with R(•) a reconstruction algorithm;
μ(•) the measure of correspondence for how well the reconstructed images match
cc(•) the count-to-path length conversion operator;
F(•,•) the weight application operator.

In embodiments, the measure μ is the least squares function of the pixelwise difference between the two images. However other suitable distance measure such as a RMS, $L^p$ norms, p other than ½, may be used instead.

At step S830, the weights or emulator weights are then output. The emulator weights w may be stored in a memory WM.

The weights may then be retrieved when imaging with the photon counting detector to applied to the count projection date if one wishes to emulate imaging capabilities of the energy integrating detector, as explained above at FIGS. 3 and FIG. 7.

It will be understood that the above described method of generating the weights can be done experimentally by imaging a test object such as phantom, and the data received at input steps S810a,b then derives from this calibration imaging procedure. Preferably, the phantom imaged to obtain the input data received at receiving step S810a,b may include plural different materials. In embodiment, the phantom includes module includes any one or more of different polymers of different densities, such as polystyrene, Teflon® and others, air enclosures an water pockets. But the method for generating the weights may also be practiced theoretically by computational simulation, such Monte Carlo methods or otherwise, based on a specification of an X-ray source, specification of the two detectors and material specifications of a, now virtual, phantom.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the interne or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for image processing, comprising:
   an input interface for receiving energy resolved count data generated by a photon-counting detector;
   a count data transformer configured to transform the energy resolved count data into transformed count data by applying one or more weights to the energy resolved count data, the weights being based on calibration image data for the photon-counting detector and the calibration image data for an energy integrating detector;
   a data convertor configured to convert the transformed count data into through-material path length data to enable the photon-counting detector to emulate the energy integrating detector; and
   an output interface for outputting the through-material path length data.

2. The system according to claim 1, wherein the data convertor is configured to convert the transformed count data into the through-material path length data based on the one or more weights as applied to the energy resolved count data.

3. The system according to claim 1, wherein the one or more weights are the same for all pixels of the photon-counting detector.

4. The system according to claim 1, further comprising a reconstructor configured to reconstruct the through-material path length data into image data.

5. The system according to claim 1, wherein a material includes water or a material having a similar radiodensity.

6. The system according to claim 1, comprising a user interface configured to allow a user to change at least one of the weights.

7. A computer-implemented image processing method, comprising:
   receiving energy resolved count data generated by a photon-counting detector;
   transforming the energy resolved count data into transformed count data by applying one or more weights to the energy resolved count data, the weights being based on calibration image data for the photon-counting detector and the calibration image data for the energy integrating detector;
   converting the transformed count data into through-material path length data to enable the photon-counting detector to emulate the energy integrating detector; and
   outputting the through-material path length data.

8. A non-transitory computer readable medium for storing executable instructions that, when executed, cause the method of claim 7 to be performed.

* * * * *